United States Patent
Möllenhoff et al.

[19]

[11] Patent Number: 6,155,064

[45] Date of Patent: Dec. 5, 2000

[54] HOUSING FOR PROTECTING MONITORING EQUIPMENT

[76] Inventors: Horst Möllenhoff, Witthausstr. 29, 45470 Mülheim, Germany; Wilhelm Rüben, Gertrudistr. 21, 47800 Krefeld, Germany; Joachim Dohmann, Westhoffstr. 51, 46149 Oberhausen, Germany; Kurt Sobotta, Bruchhausener Str. 2, 53819 Neunkirchen-Seelscheid, Germany

[21] Appl. No.: 09/286,066

[22] Filed: Apr. 5, 1999

[30] Foreign Application Priority Data

Apr. 9, 1998 [DE] Germany .......................... 198 15 975

[51] Int. Cl.[7] .................................................. F25D 23/12
[52] U.S. Cl. ......................................................... 62/259.2
[58] Field of Search .......................... 62/259.2; 361/600, 361/678, 688

[56] References Cited

U.S. PATENT DOCUMENTS

| | | | |
|---|---|---|---|
| 4,207,541 | 6/1980 | Karger et al. .................. 331/94.5 P |
| 4,796,143 | 1/1989 | Odenkirchen et al. ................... 361/37 |
| 5,616,973 | 4/1997 | Khazanov et al. ......................... 310/54 |
| 5,986,210 | 11/1999 | Kummle et al. .......................... 174/59 |

FOREIGN PATENT DOCUMENTS 2-64384  3/1990  Japan .................................... 62/259.2

*Primary Examiner*—William Doerrler
*Assistant Examiner*—Mel Jones
*Attorney, Agent, or Firm*—Max Fogiel

[57] ABSTRACT

A housing for protecting monitoring equipment employed to maintain watch over dusty environments. The housing comprises a cylindrical jacket (1) that accommodates the equipment. The front of the jacket is closed except for one or more apertures (12) and extends into the environment being monitored. The housing is provided with a connection (10) for a coolant or flush in the form of air. One or more outlets (15 & 17) communicate with the inside of the housing in the vicinity of the aperture and are oriented such that the air emerging from the outlets forms a cushion between the aperture and the environment being monitored.

6 Claims, 1 Drawing Sheet

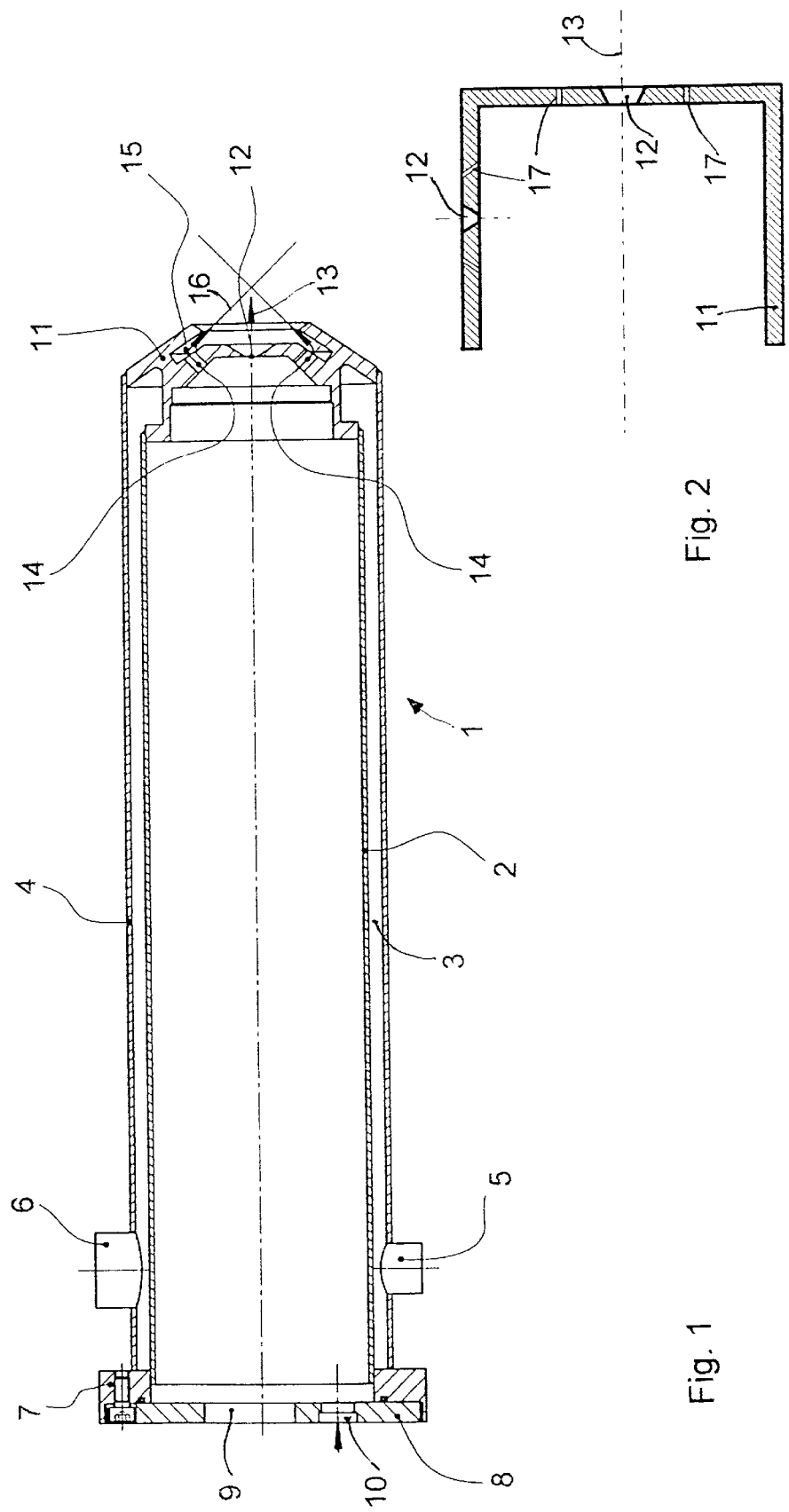

HOUSING FOR PROTECTING MONITORING EQUIPMENT

The present invention concerns a housing for protecting monitoring equipment employed to maintain watch over dusty environments and having the characteristics recited in the preamble to claim 1.

Known housings for protecting electronic sensors like CCD or infrared cameras and other monitoring equipment employed in such dusty environments as the furnaces in incineration plants are flushed with air to cool the optical systems at the front (Gaswärme International 46 [1997], 10, 479–83). The air is conveyed through the housing and leaves through an aperture about 1 to 4 mm in diameter at the front. The air is compressed to 1 to 1.5 bars inside the housing. The compression also helps keep any particles of dust or ash in the furnace out of the housing. The outermost lens is accordingly kept clean.

The drawback of such housings is that the drop in pressure just outside the aperture allows solid particles to accumulate there over eight to 24 hours, depending on the dimensions of the furnace, requiring thorough cleaning at frequent intervals. Malfunctions can even occur early in the operation. The equipment must be removed to clean it, interrupting the monitoring. The outermost lens can also be damaged if the aperture is cleaned frequently.

The object of the present invention is accordingly a housing of the aforesaid genus with an aperture that will long remain free of dust from the environment being monitored.

This object is attained in accordance with the present invention in a housing of the aforesaid genus by the characteristics recited in the body of claim 1.

The cushion created by the air leaving the housing through the outlets acts as a barrier and prevents particles of dust from the environment being monitored from accumulating at the aperture. The aperture is kept free of dust, and the housing will not need to be cleaned for quite a while.

Several embodiments of the present invention will now be specified with reference to the accompanying drawing, wherein FIG. 1 is a longitudinal section through a housing for protecting monitoring equipment and FIG. 2 illustrates the front of another embodiment.

The housing for protecting monitoring equipment has a cylindrical jacket 1 that accommodates the unillustrated equipment. When employed in high heat, at a temperature of 1800° for example, jacket 1 will need to be cooled and will accordingly have an inner wall 2 loosely surrounded by an outer wall 4 with coolant, water for instance, flowing through the cylindrical gap 3 left between them. Outer wall 4 will in this event be provided with an inlet 5 and an outlet 6 for the coolant.

Such a refrigerated jacket 1 will be sealed water-tight with an O ring 7 at the back, and a removable cap 8 will be screwed over the ring. Cap 8 will be provided with a central and tightly sealed port 9 for electrical connections and with a connection 10 to admit air for flushing out the housing. This air is compressed to 1 to 1.5 bars above the air in the environment being monitored.

The front, the end of the jacket 1 that extends into the environment being monitored, in one embodiment is in the form of a conical head 11 fastened liquid-tight to inner wall 2 and outer wall 4 and incorporated into the coolant-circulation system. The head in another embodiment, however, is flat and in the same plane as the wall of the monitored environment.

The head 11 is provided with a central aperture 12 outside the outermost lens in the housing's unillustrated optical system and opening toward the environment being monitored. The air flowing through the housing leaves it through aperture 12 along an axis 13 and at a pressure above that inside the monitored environment, preventing dust-laden gas from entering the housing from the environment. Without the measures that will now be specified, however, the air leaving aperture 12 would suction up dust-laden gas from its vicinity, and solid particles would reach aperture 12 and contaminate it.

Head 11 is accordingly specially designed fluidically to prevent contamination of inner wall 2. The head 11 in the embodiment illustrated in FIG. 1 for instance is provided with several bores 14 arranged in an arc and leading into a continuous annular depression 15 in the vicinity of aperture 12 that opens toward the environment being monitored and constitutes an outlet for the air at that point. The axis 16 of depression 15 slopes in relation to the axis 13 of aperture 12 and intersects it at a point remote from the aperture. Although the axis 16 in the present embodiment intersects axis 13 at 45°, the angle can be more acute and even 0°. The air leaving depression 15 will accordingly create a cushion that will keep dust-laden gas away from aperture 12. Bores 14 can also slope slightly to generate a tangential vortex.

FIG. 2 illustrates another type of fluidically designed head 11. The housing in this embodiment is cooled, not by liquid, but only by the air flowing through it. Aperture 12 can be provided at either the front or the side of jacket 1 and is surrounded by several outlets 17, paralleling or at an angle to the aperture's axis.

What is claimed is:

1. Housing for protecting monitoring equipment employed to maintain watch over dusty environments and comprising a cylindrical jacket (1) that accommodates the equipment, whereby the front of the jacket is closed except for one or more apertures (12) and extends into the environment being monitored and whereby the housing is provided with a connection (10) for a coolant or flush in the form of air characterized by one or more outlets (15 & 17) communicating with the inside of the housing in the vicinity of the aperture and oriented such that the air emerging from the outlets forms a cushion between the aperture and the environment being monitored.

2. Housing as in claim 1, characterized in that the axes (16) of the outlets (15 & 17) slope toward the axis (13) of the aperture (12) such that the axes intersect axially remote from the aperture.

3. Housing as in claim 1, characterized by several bores (14) through its front that open into a continuous annular depression that constitutes the outlet.

4. Housing as in claim 1 characterized in that the axes (16) of the outlets (15 & 17) slope radially toward the axis (13) of the aperture (12) and have components that slope slightly toward its circumference.

5. Housing as in claim 1, characterized in that the jacket (1) has two walls and has a coolant flowing between them.

6. Housing as in claim 1, characterized in that its front is conical.

* * * * *